United States Patent [19]

Breder, Jr.

[11] Patent Number: 4,544,787

[45] Date of Patent: Oct. 1, 1985

[54] PREPARATIVE PROCESS FOR SUPPORTS

[75] Inventor: E. William Breder, Jr., Oak Forest, Ill.

[73] Assignee: Atlantic Richfield Company, Philadelphia, Pa.

[21] Appl. No.: 600,926

[22] Filed: Apr. 16, 1984

[51] Int. Cl.[4] ............................................. C07C 2/00
[52] U.S. Cl. .................................. 585/500; 585/400; 585/417; 585/541; 585/654; 585/658; 585/700; 585/943
[58] Field of Search ............... 585/415, 417, 418, 500, 585/541, 654, 656, 658, 661, 943, 700

[56] References Cited

U.S. PATENT DOCUMENTS

| | | | |
|---|---|---|---|
| 4,205,194 | 5/1980 | Mitchell, III et al. | 585/500 |
| 4,239,658 | 12/1980 | Mitchell, III et al. | 585/500 |
| 4,443,645 | 4/1984 | Jones et al. | 585/500 |
| 4,443,648 | 4/1984 | Jones et al. | 585/500 |

OTHER PUBLICATIONS

Fang, T. and Yeh, C., "Catalytic Pyrolysis of Methane," J. of Chinese Chem. Soc., 29, 265–273 (1981).
Keller, G. E. "Synthesis of Ethylene via Oxidative Coupling of Methane", J. of Catalysis, 73, 9–19 (1982).

*Primary Examiner*—William R. Dixon, Jr.
*Assistant Examiner*—Cynthia A. Prezlock
*Attorney, Agent, or Firm*—Donald L. Traut

[57] ABSTRACT

An improved process for the production of a contact agent comprising digesting a reducible oxide of at least one metal, the oxide of which forms a reduced metal oxide, and a support in the presence of a silicon component, drying the precipitate of the reducible oxide and calcining the precipitate to form the contact agent.

5 Claims, No Drawings

PREPARATIVE PROCESS FOR SUPPORTS

BACKGROUND OF THE INVENTION

1. Field of the Invention

This invention relates to the synthesis of hydrocarbons from a methane source. A particular application of this invention is a method for converting natural gas to more readily transportable material using a methane conversion catalyst. More particularly, this invention relates to an improved preparative process for a methane conversion catalyst.

2. Description of the Pertinent Art

A major source of methane is natural gas. Other sources of methane have been considered for fuel supply (e.g., the methane present in coal deposits or formed during mining operations). Relatively small amounts of methane are also produced in various petroleum processes.

The composition of natural gas at the wellhead varies, but the major hydrocarbon present is methane. For example, the methane content of natural gas may vary within the range of about 40 to about 95 volume percent. Other constituents of natural gas include ethane, propane, butane, pentane (and heavier hydrocarbons), hydrogen sulfide, carbon dioxide, helium, and nitrogen.

Natural gas is classified as dry or wet, depending upon the amount of condensable hydrocarbons contained in it. Condensable hydrocarbons generally comprise $C_3+$ hydrocarbons, although some ethane may be included. Gas conditioning is required to alter the composition of wellhead gas; processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting and revaporizing natural gas are complex, energy intensive and require extensive safety precautions. Transport of natural gas has been a continuing problem in the exploitation of natural gas resources. It would be extremely valuable to be able to convert methane (e.g., natural gas) to more readily transportable products. Moreover, direct conversion to olefins such as ethylene or propylene would be extremely valuable to the chemical industry.

Recently, it has been discovered that methane may be converted to higher hydrocarbons by a process which comprises contacting methane and an oxidative synthesizing agent at synthesizing conditions (e.g., at a temperature selected within the range from about 500° to about 1000° C.). An oxidative synthesizing agent is a composition having as a principal component at least one oxide of at least one metal, which composition produces $C_2+$ hydrocarbon products, water and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony and bismuth are most useful. Important in the utilization of the reducible metal oxide is the selection of a support material. Magnesia has been the preferred support for most applications.

Accordingly, an object of this invention is to provide an improved process for converting methane to higher hydrocarbons. A further object of this invention is an improved oxidative synthesizing agent—one capable of converting methane with reduced byproduct selectivities. A still further object of this invention is an oxidative synthesizing agent with improved stability—an agent that maintains desirable conversion properties for longer periods of time.

Other aspects, objects and the several advantages of this invention will become apparent to those skilled in the art upon reading this Specification and the appended claims.

SUMMARY OF THE INVENTION

It has now been found that the conversion of methane to higher hydrocarbons is improved by a contact agent produced by the method having the following steps:
(a) combining hydroxylated magnesia and a component of silicon which forms silica and which is readily suspendible in a continuous medium;
(b) contacting the combined components with a component of at least one metal, the oxide of which is reducible; and
(c) calcining the contacted components to form the contact agent.

The term hydroxylated magnesia means a magnesia derived from magnesium hydroxide or a magnesium-containing component contacted with a hydroxyl-containing material.

DETAILED DESCRIPTION OF THE INVENTION

It has been found that a superior contact agent may be prepared using a reducible metal oxide supported by magnesia or a magnesia-containing material which contains silica.

The contact agent of the present invention comprises at least one reducible oxide of at least one metal, which reducible oxide when contacted with methane at at a temperature selected within the range of about 500° to about 1000° C. produces higher hydrocarbon products, water and a reduced metal oxide. The term "reducible" is used to identify those oxides of metal which are reduced by the methane contact. The term "oxide(s) of metal(s)" includes: (1) one or more metal oxides (i.e., compounds described by the general formula $M_xO_y$ wherein M is a metal, O is oxygen, and the subscripts x and y designate the relative atomic proportions of metal and oxide in the composition); and/or (2) one or more oxygen-containing metal compounds; provided that such oxides and compounds have the capability of performing to produce higher hydrocarbon products as set forth herein.

The preferred agents comprise reducible oxides of metals selected from the group consisting of manganese, tin, indium, germanium, antimony, lead, bismuth, and mixtures thereof. The particularly preferred agents comprise reducible oxides of manganese and mixtures of reducible oxides of manganese with other agents.

The hydroxylated magnesia is preferably derived from magnesium hydroxide, e.g. magnesia produced from sea water. One such suitable magnesia is commercially available from CRI Industries as MgO-700.

Alternatively, the hydroxylated magnesia may be derived from sources other than magnesium hydroxide, such as a magnesium-containing component contacted with hydroxyl-containing material (e.g., one or more compounds including hydroxyl groups). Such hydroxyl-containing materials include sodium hydroxide, potassium hydroxide, lithium hydroxide, slaked lime, calcium hydroxide, and hydroxides of barium. One method of producing the present hydroxylated magnesia comprises contacting a magnesium-containing component with (a) water for an extended period or (b) boiling water. Any suitable magnesium-containing component may be employed to produce hydroxylated magnesia. Examples include magnesia, magnesium chloride, and magnesium salts.

The combined components may be contacted with the metal component during the combining step by digestion, or after by digestion or impregnation.

A suitable method of preparation of the agent is to digest a component of a silicon and a hydroxylated magnesia in an aqueous medium. Following drying the combined components, the solid is contacted, as by impregnating, with a solution of a compound, such as sodium permanganate, of a metal, which forms at least one reducible oxide. Preferably, the silicon component comprises about 5 to about 15 weight percent of the aqueous combined components, and more preferably about 10 weight percent of the combined components.

The contacted components, which are preferably dried, are calcined to yield the contact agent. Preferably, the components are maintained in contact with at least a portion of the liquid phase for up to 24 hours prior to removal and drying.

Drying and calcination may take place simultaneously. However, it is preferred that the drying take place at a temperature below that at which water of hydration is removed from the contacted components. Thus, this drying may occur in flowing air at temperatures below about 500° F., preferably in the range of about 150° to about 450° F., more preferably about 230° to about 450° F. Alternatively, the contacted components can be spray dried.

The drying of the contacted components can be accomplished in various manners; for example, by spray drying, drum drying, flash drying, tunnel drying, and the like. The drying temperature or temperatures are selected to remove at least a portion of the liquid phase. Drying times are not critical to the present invention and may be selected over a relatively wide range sufficient to provide the desired dried product. Drying times in the range of about 0.2 to about 24 hours or more may be advantageously employed. Preferably, the contacted components are spray dried to form particles of the agent having a particle diameter ranging from about 20 to about 125 microns.

Spray drying equipment which is conventionally used to produce catalyst particles suitable for use in fluidized bed reactors may be utilized in the practice of the present invention. For example, this equipment may involve at least one restriction or high pressure nozzle having a diameter in the range of about 0.01 to about 0.2 inch, preferably about 0.013 to about 0.15 inch. The pressure upstream of this high pressure nozzle may range from about 400 psig to about 10,000 psig, preferably from about 400 psig to about 7,000 psig. The material to be dried is sent through the nozzle system into a space or chamber. The pressure in the space or chamber downstream from the nozzle system is lower than that immediately upstream of the nozzle and is typically in the range of about 0 psig to about 100 psig, preferably about 0 psig to about 20 psig. Once through the nozzle, the material to be dried is contacted for a relatively short time (e.g., about 0.1 second to about 20 seconds) with a gas stream which is at a temperature of about 200° to about 1500° F., preferably about 200° to about 750° F. The gas stream, which may be, for example, air or the flue gases from an inline burner (used to provide a gas stream having the proper temperature) or a substantially oxygen-free gas, may flow co-current, counter-current or a combination of the two relative to the direction of flow of the material to be dried. The spray drying conditions, such as temperature, pressure and the like, may be adjusted because, for example, of varying the composition of the material to be dried to obtain optimum results. However, this optimization may be achieved through routine experimentation.

An alternative to the high pressure nozzle described above is the two-fluid nozzle in which the material to be dried is dispersed by a stream of gas, typically air. The two-fluid nozzle has the advantage of low operating pressure, e.g., about 0 psig to about 60 psig for the material to be dried and about 10 psig to about 100 psig for the dispersing gas. The dispersing gas may also function as at least a portion of the drying gas stream. The various operating parameters noted above may be varied in order to achieve the correct or desired bound particle size.

In order to minimize contact between the chamber walls and the wet material, the chamber downstream from the nozzle system is large in size (e.g., about 4 to about 30 feet in diameter and about 7 to about 30 feet long) often with an additional conical shaped portion for convenient withdrawal of the dried material. The spray drying apparatus may also include separation means (e.g., cyclone separators) in the outlet gas line to recover at least a portion of the dried material entrained in this stream.

Suitable calcination temperatures for the contact solid are in the range of about 300° to about 1200° F. However, it has been found that improved agent formation occurs when the calcination temperature is maintained within the range of about 300° to about 1200° F. Calcination of the contact solid may take place in a period of time in the range of about 0.5 to about 24 hours or more, preferably in a period of time in the range of about 1 to about 10 hours. The calcination of the contact solid may occur under any suitable conditions, e.g., inert, reducing or oxidizing conditions, the oxidizing conditions being preferred. Particular calcination temperatures will vary, depending upon the particular metal compound or compounds employed.

The preferred contact agent of this invention contains, in addition to the foregoing elements, at least one alkali metal. The atomic ratio in which these materials are combined to form the contact agent is not narrowly critical. However, the preferred atomic ratio of the reducible oxide component (expressed as the metal, e.g., Mn) to the alkali metal component (expressed as the metal, e.g., Na) is within the range of about 0.1:1 to about 100:1, more preferably within the range of about 0.3:1 to about 10:1. Preferably alkali metals include sodium and lithium.

The process of this invention provides a contact agent composition exhibiting surface areas ranging from about 25 to about 600 square meters per gram.

In addition to methane, the preferred feedstock employed in the method of this invention may contain other hydrocarbon or non-hydrocarbon components, although the methane content should typically be within the range of about 40 to about 100 volume percent, preferably about 80 to about 100 volume percent, more preferably about 90 to about 100 volume percent.

Operating temperatures for contacting the methane with the contact agent are selected within the range of about 500° to about 1000° C.; the particular temperature selected depending upon the particular reducible metal oxide(s) employed in the oxidative synthesizing agent. For example, reducible oxides of certain metals may require operating temperatures below the upper part of the recited range to minimize sublimation or volatilization of the metals (or compounds thereof) during methane contact. Examples include reducible oxides of indium germanium and bismuth (operating temperatures will preferably not exceed about 850° C.).

Operating pressures for the methane contacting step are not critical to the presently claimed invention. However, both general system pressure and partial pressure of methane have been found to affect overall results. Preferred operating pressures are within the range of about 1 to about 30 atmospheres.

Contacting methane and a reducible metal oxide to form higher hydrocarbons from methane also produces reduced metal oxides and water. The exact nature of the reduced metal oxides is unknown and so is referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to about 1200° C.; the particular temperature selected depending on the metal(s) included in the contact agent.

In carrying out the present process, a single reactor apparatus containing a fixed bed of solids may be used with intermittent or pulsed flow of a first gas comprising methane followed by intermittent or pulsed flow of a second gas comprising oxygen (e.g., oxygen, oxygen diluted with an inert gas, or air, preferably air). The methane contacting step and the oxygen contacting step may also be performed in physically separate zones with solids recirculating between the two zones.

Thus, a suitable method for synthesizing hydrocarbons from a methane source comprises: (a) contacting a gas comprising methane and particles comprising a contact agent to form higher hydrocarbon products, water and reduced metal oxide; (b) removing particles comprising reduced metal oxide from the first zone and contacting the reduced particles in a second zone with an oxygen-containing gas to form particles comprising a contact agent; and (c) returning the particles produced in the second zone to the first zone. The steps are preferably repeated at least periodically, and more preferably the steps are continuous. In the more preferred embodiment, solids are continuously circulated between at least one methane contact zone and at least one oxygen contact zone.

Particles comprising a reducible metal oxide which are contacted with methane may be maintained as fluidized, ebullating, or entrained beds of solids. Preferably, methane is contacted with a fluidized bed of solids.

Similarly, particles comprising reduced metal oxide which are contacted with oxygen may be maintained as fluidized, ebullating, or entrained beds of solids. Preferably, oxygen is contacted with a fluidized bed of solids.

In the more preferred embodiment of the present invention, methane feedstock and particles comprising a contact agent are continuously introduced into a methane contact zone maintained at synthesizing conditions. Synthesizing conditions include the temperatures and pressures described above. Gaseous reaction products from the methane contact zone (separated from entrained solids) are further processed (e.g., passed through a fractionating system wherein the desired hydrocarbon products are separated from unconverted methane and combustion products). Unconverted methane may be recovered and recycled to the methane contact zone.

Particles comprising reduced metal oxide are contacted with oxygen in an oxygen contact zone for a time sufficient to oxidize at least a portion of the reduced metal oxide to produce a reducible metal oxide and to remove (i.e., combust) at least a portion of any carbonaceous deposit which may form on the particles in the methane contact zone. The conditions of the oxygen contact zone will preferably include a temperature selected within the range of about 300° to about 1200° C., pressures of up to about 30 atmospheres, and average particle contact time within the range of about 1 to about 120 minutes. Sufficient oxygen is preferably provided to oxidize all reduced metal oxide to produce a reducible metal oxide and to completely combust any carbonaceous deposit material deposited on the particles. At least a portion of the particles comprising the contact agent which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady state operation of the synthesizing system.

While this invention has been described with respect to various specific examples and embodiments, it is to be understood that the invention is not limited thereto and that it can be variously practiced within the scope of the following claims.

What is claimed is:

1. In an improved method for converting a gas comprising methane to higher hydrocarbons which comprises contacting said gas with a contact agent, said contact agent comprising a component of at least one metal, the oxide of which is reduced and produces higher hydrocarbons and water when contacted with methane at selected temperatures within the range of about 500° to about 1000° C., the improvement which comprises employing said contact agent produced by the steps of:
    (a) combining hydroxylated magnesia and a component of silicon which forms silica and is readily suspendible in a continuous medium;
    (b) contacting said combined components with said component of at least one metal; and
    (c) calcining said contacted components to form said contact agent.

2. The method of claim 1 wherein said at least one metal is selected from a group consisting of manganese, tin, indium, germanium, antimony, lead, bismuth, and mixtures thereof.

3. The method of claim 1 wherein said silicon component is suspended as a gel or a solution.

4. The method of claim 3 wherein said silicon component is selected from a group consisting of colloidal silica, sodium silicate, and mixtures thereof.

5. The method of claim 4 wherein said silicon component comprises between about 5 and about 15 weight percent of said combined components.

\* \* \* \* \*